United States Patent [19]

Hubbard

[11] Patent Number: 4,661,455
[45] Date of Patent: Apr. 28, 1987

[54] MEMBRANE CELL CULTURING DEVICE
[75] Inventor: Peter J. Hubbard, Darien, Conn.
[73] Assignee: Dorr-Oliver Incorporated, Stamford, Conn.
[21] Appl. No.: 819,762
[22] Filed: Jan. 16, 1986
[51] Int. Cl.[4] .............. C12N 5/00; C12M 1/14
[52] U.S. Cl. .................. 435/240; 435/285; 435/310
[58] Field of Search .............. 435/284, 285, 286, 287, 435/300, 301, 309, 310, 313, 240, 71, 813

[56] References Cited

U.S. PATENT DOCUMENTS

| | | | |
|---|---|---|---|
| 2,222,651 | 11/1940 | Breuchaud | 435/310 |
| 3,734,851 | 5/1973 | Matsumura | 435/285 |
| 3,948,732 | 4/1976 | Haddad et al. | 435/285 |
| 3,997,396 | 12/1976 | Delente | 435/285 |
| 4,201,845 | 5/1980 | Feder et al. | 435/285 |
| 4,225,671 | 9/1980 | Puchinger | 435/285 |

*Primary Examiner*—James C. Young
*Attorney, Agent, or Firm*—Paul D. Greeley; Burtsell J. Kearns; Gary R. Plotecher

[57] ABSTRACT

The present invention provides a novel apparatus for culturing mammalian cells, whereby a plastic housing encasing a double membrane bag or bags supplies nutrients and oxygen to mammalian cells for propagation thereof. The double membrane bag contains a first bag formed of a microfiltration or ultrafiltration membrane disposed within a second membrane bag formed of a liquid impermeable, gas permeable membrane. This apparatus has a first chamber containing oxygen, a second chamber containing cells and a third chamber containing nutrients.

20 Claims, 13 Drawing Figures

FIG. 7
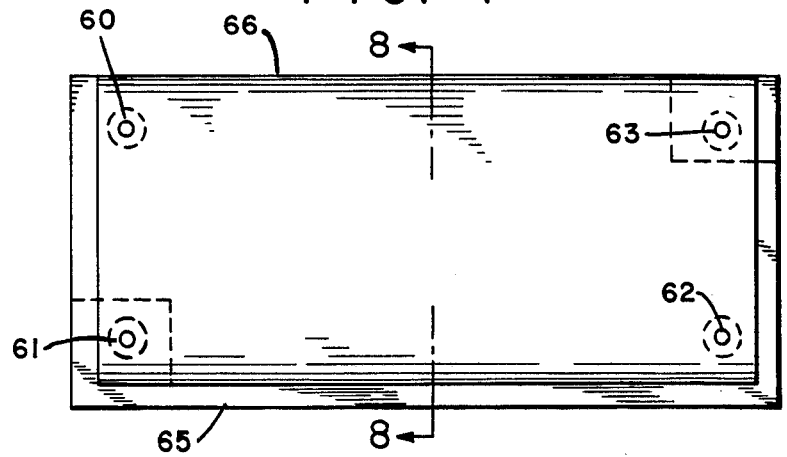
FIG. 8
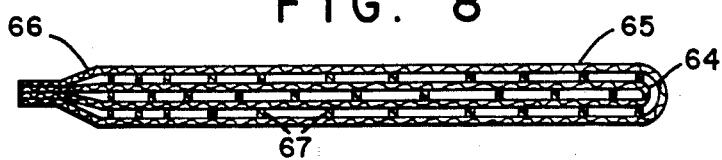
FIG. 8A
FIG. 9
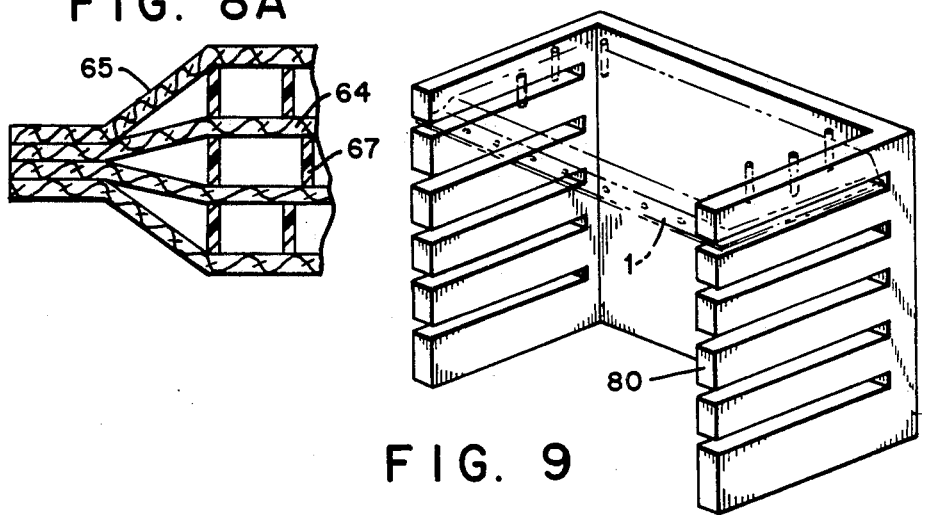

MEMBRANE CELL CULTURING DEVICE

BACKGROUND OF THE INVENTION

The present invention relates to a novel device for culturing cells using a first membrane forming a first bag, having a spacer material disposed within the first bag so as to maintain each side of the first bag at a predetermined distance from the opposing side; a second membrane forming a second bag containing therein the first bag, having a spacer material disposed within the second bag so as to maintain a predetermined distance between the interior surface of the second bag and the exterior surface of the first bag; a housing which encases the first and second bags; and three inlets and outlets disposed therein for passing a gas, cell culture and cell nutrient into selected chambers formed thereby.

There has been increased interest in recent years in methods for the culturing of in-vitro cells, especially mammalian cells. It is generally known that cells require both oxygen and nutrients to propagate and flourish. Recognizing such requirements a number of devices have been designed attempting to cultivate in-vitro cells in environments of oxygen and nutrients simultaneously.

U.S. Pat. No. 3,997,396 describes one method for the propagation of living cells in-vitro by attaching and growing cells on one side or surface of a hollow fiber membrane, and by passing oxygen through the membrane from the other side in contact with the cells and simultaneously incubating the cells in a nutrient medium. Another device is described in U.S. Pat. No. 3,948,732 which describes a replaceable, sterilizable, cell growth assembly comprising a chamber structure of gas permeable, liquid impermeable material having an inner surface to which cells are attachable. The chamber is of a tubing configuration and is disposed in a plurality of layers in stacked relation. The spacer structures between the layers of tubing define a plurality of flow passages between the layers and enable a gaseous environment to bath the majority of the external surface area of the tubing layers. The chamber also includes an inlet conduit for introducing a culture media for flow-thru the plural layers of the chamber structures and an outlet conduit for receiving culture media from the chamber structures, and coupling structures for detachably connecting the inlet conduit to a source of culture media and the outlet conduit to an appropriate culture media receptacle.

U.S. Pat. No. 4,225,671 describes a process for the in-vitro biosynthesis of hormones, especially insulin, by producing the cells in one or more cell culture spaces separated by semipermeable flat membranes such that there is at least one cell culture space surrounded by cell media (nutrient) and gas. U.S. Pat. No. 4,225,671 demonstrates multiple layering of gas, cell culture, and cell media spaces by connecting the gas and cell media in series with other gas and cell media spaces and also by connecting the cell culture spaces in parallel with other cell culture spaces. This is accomplished by means of flat plate type membranes being stacked one on top of the other for forming spaces therein.

The problem with the aforementioned devices is the amount of dead space between the membrane plates which result in some cells receiving less oxygen and nutrients than others. Moreover, they require numerous external fittings for the inlets and outlets which can result in leakage, loss of cells and increased capital cost. These systems are also bulky in size, i.e. they take up to much space in the laboratory, which requires increasing the means for pumping nutrient, gas and cells therethrough thus generating undesirable increases in heat from the larger pumping means. Increases in heat is unacceptable in culturing of mammalian cells or the like due to the pristine conditions required for propagation of the cells.

The present inventors developed an apparatus which overcomes the aforementioned channel spacing and dead space problems, as well as providing a cell culturing apparatus of reduced size and complexity.

SUMMARY OF THE INVENTION

It is a primary object of the present invention to provide an apparatus for growing cells, such as mammalian plant cells, comprising:

a first membrane forming a first bag, having a spacer material disposed within the first bag so as to maintain each side of the first bag at a predetermined distance from the opposing side;

a second membrane forming a second bag containing therein the first bag, having a spacer material disposed within the second bag so as to maintain a predetermined distance between the interior surface of the second bag and the exterior surface of the first bag;

a housing which encases the first and second bags;

a first inlet disposed in at least a wall of the housing such that it is only in flow communication with a first chamber defined between the interior surface of the housing and the exterior surface of the second bag;

a second inlet disposed in at least a wall of the housing and second bag such that it is only in flow communication with a second chamber defined between the exterior surface of the first bag and the interior surface of the second bag;

a third inlet disposed in at least a wall of the housing, the first bag and the second bag such that it is only in flow communication with a third chamber defined within the interior surface of the first bag;

a first outlet disposed in at least a wall of the housing, such that it is only in flow communication with the first chamber;

a second outlet disposed in at least a wall of the housing, and the second bag such that it is only in flow communication with the second chamber; and a third outlet disposed in the housing, first bag and second bag, such that it is only in flow communication with the third chamber.

Furthermore, it is an object of the present invention wherein the first membrane is sealed at its end to form the first bag and the second membrane is sealed at its end to form the second bag. The ends of both the first and second membranes may also be sealed together by heat treatment to form a double bag having the first bag enclosed within the second bag.

Another object of the present invention is to provide a number of double bags in series or in parallel with each other encased within a single housing to increase the flow-thru and production of each housing unit.

It is also an object of the present invention wherein the first membrane is either a microfiltration or ultrafiltration membrane and the second membrane is a gas permeable, liquid impermeable membrane. Conversely, the first membrane may instead be gas permeable, liquid impermeable membrane and the second membrane may be either a microfiltration or ultrafiltration membrane depending on the preference or the need of the producer. A gas permeable, liquid impermeable membrane such as a dimethyl silicone gas membranes can be used.

When a first membrane is a microfiltration membrane and the second membrane is a gas permeable, liquid impermeable membrane oxygen can be introduced to the first chamber via the first inlet; cells are introduced into the second chamber via the second inlet; and a cell nutrient is introduced into the third chamber via the third inlet. Similarly, oxygen, cells and nutrients are removed from the aforementioned chambers via the first, second and third outlets, respectively.

Additionally, it is an object of the present invention that when the first membrane is a gas permeable, liquid impermeable membrane and the second membrane is a microfiltration membrane that cell nutrient is introduced into the first chamber via the first inlet, cells are introduced into the second chamber via the second inlet, and oxygen is introduced into the third chamber via the third inlet.

It is a further object of the present invention wherein the inlets and outlets are hollow tubes sealed at one end and open at the other end. The hollow tubes also have openings, within their side walls, the openings being near the sealed end and within the housing. Additionally, it is an object wherein gaskets or seals are provided at the point where the inlets and outlets penetrate the housing, the first membrane bag and the second membrane bag, the gaskets being arranged such that the first inlet and outlet are only in flow communication with the first chamber, the second inlet and outlet are only in flow communication with the second chamber and the third inlet and outlet are only in flow communication with the third chamber, whereby leakage into the other chambers is avoided.

Furthermore, it is also an object to provide a method for growing cells using the apparatus of the present invention.

An additional object of the present invention is to provide bolts or stainless steel elongated spring clamps along the edges of the housing to secure the individual parts thereof so as to avoid leakage.

It is also an object of the present invention that a nylon threaded screw secured by a nut may be used as the inlets and outlets. If a nylon screw is used a hole may be drilled from the head thru the tip of the screw such that the nutrient, gas or cell may come right out the top of the head and into either the first, second or third chambers as desired. The use of the nylon screw or button requires less gaskets and results in reduced leakage.

The present invention may also include many additional feature which shall be further described below.

BRIEF DESCRIPTION OF THE DRAWINGS

FIG. 7 is a top perspective view of a double bag according to the present invention;

FIG. 8 is a cross-sectional view taken along line 8—8 of FIG. 7;

FIG. 8a is a cut-out of the sealed ends of the first and second bags of FIG. 8;

FIG. 9 is a perspective view from the top right of a rack for holding numerous biopac units according to the present invention;

DESCRIPTION OF THE PREFERRED EMBODIMENT

Figure 1:
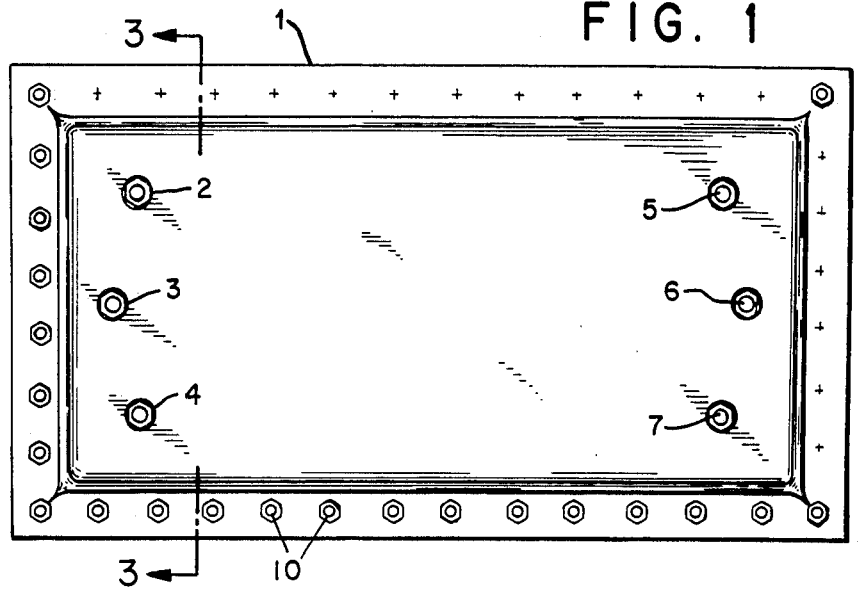
FIG. 1 is a top planner view of the apparatus according to the present invention.

The present invention provides a novel method and apparatus for growing cells, the apparatus having a first membrane and a second membrane. The first membrane forming a first bag having a spacer material disposed therein so as to maintain the opposite sides of the bag at a predetermined distance from each other. The second membrane forming a second bag which contains the first bag in its interior. The second bag having a spacer material disposed therein so as to maintain a predetermined distance between the interior surface of the second bag and the exterior surface of the first bag.

The apparatus according to the present invention provides a housing, which may be made from any liquid and gas impervious material, which encases the first and second bags therein. A first inlet is disposed in the housing such that it is only in flow communication with a first chamber defined between the interior surface of the housing and the exterior surface of the second bag. A second inlet is disposed in at least a wall of the housing and the second bag such that it is only in flow communication with a second chamber defined between the exterior surface of the first bag and the interior surface of the second bag. A third inlet disposed in at least a wall of the housing, the first bag and the second bag such that it is only in flow communication with a third chamber defined within the interior surface of the first bag. The aforementioned inlets have corresponding outlets which are also in flow communication with their respective chambers. This permits easy flow-thru movement of any nutrients, gas or cells that are inserted into the apparatus through the inlets.

The basic concept of this apparatus is to simulate cell culturing conditions like a mammalian body where cells are in close proximity to oxygen and nutrient in order to propagate. For this reason the double bag of the present invention was designed by the present inventor to incorporate close proximity of the cells, oxygen and nutrients normally associated with the parallel plate design along with the controllability and effectiveness of membrane bags.

According to the present invention, the cells migrate through, for example, a one millimeter channel which has a dimethyl silicon gas membrane on one side and a microfiltration or ultrafiltration membrane on the other side. In this way the cells are a short distance from the nutrients and oxygen needed for propagation. The microfiltration or ultrafiltration membrane serves the purpose of supplying the cells with nutrients and also serves as a means of extracting the by-products of the cells and carrying away the by-products along with nutrient out of the apparatus through an outlet for further downstream separation. The apparatus, according to the present invention can obtain high cell densities of $1 \times 10^8$ per milliliter or greater. A unique feature of this apparatus is that it can be linked in series or in parallel with additional double bag units to obtain larger systems without greatly increasing the space requirements for the system.

Another unique feature of the present invention is that of the unique inlet and outlet ports provide relatively leak proof means for flowing the appropriate cells, nutrients and gases there-through. It is these inlet and outlet ports which permit the use of double bag membranes, either singularly or in series, which in-turn provides significantly greater cell production rates in less space and with far less power needed to circulate the cells, nutrient and gas than the prior art apparatuses.

Maintaining a predetermined distances between the membrane walls is accomplished by a spacer grid, such as a plastic "vexar" flow spacer which permits flow-through communication between the inlets and outlets as well as controlling the space between the membranes so that cells will receive sufficient oxygen and nutrient.

The double bag of the present invention includes an inner bag made out of a silicon membrane which has a fairly high gas permeability and liquid impermeability, and an outer bag being an ultrafiltration or microfiltration membrane which serves the purpose of retaining cells and supplying nutrient to them. The cells, which are located in the space between the ultrafiltration membrane and the silicon membrane, are supplied on the inside with oxygen and the outside with nutrient. Conversely, the double bag according to the present invention may have a first bag constructed of the ultrafiltration or microfiltration membrane being encased by a second bag made of gas permeable silicon, or the like. In this instance, the cells would still be located in the space between the first bag and the second bag but the nutrient would be contained within the first bag and the gas would be provided from the exterior of the second bag. Thus, the cells which are located in the space between the ultrafiltration membrane and the silicon membrane are supplied on the inside with nutrient and on the outside with oxygen.

Another embodiment of the present invention is provided whereby a stacked pile of double bag membranes are connected in series and/or parallel so that the cells can be freely recirculated between the bags so that they can obtain sufficient amounts of nutrient and oxygen resulting in increased cell propagation. In this regard, double bags are stacked one on top of the other with common entry and exit ports for each of the nutrient, gas and cell chambers. For example, one-third of a square meter of surface area can be provided by combining four double bag membranes in series or parallel with three sets of inlet and outlet ports. According to the present invention, the housing can be constructed of polycarbonate or suitable material which are autoclavable.

Figure 2:
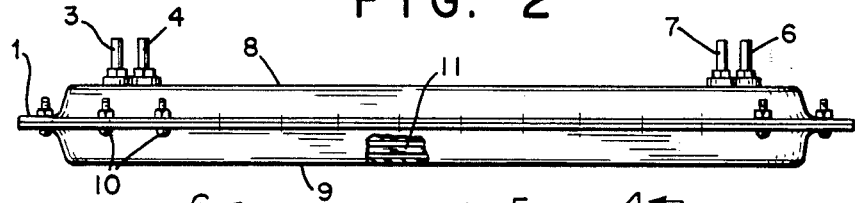
FIG. 2 is a side perspective view of the present invention.

Referring now to the figures, FIG. 1 is a top planner view of the apparatus according to the present invention having a housing 1, inlets 2, 3 and 4, and outlets 5, 6 and 7. FIG. 2 is a side perspective view of FIG. 1 showing a cut-out portion. Housing 1 consists of a top plate 8 and a bottom plate 9 secured to each other via nuts and bolts 10 or by stainless steel elongated spring channels, not shown in the drawings.

Figure 3:
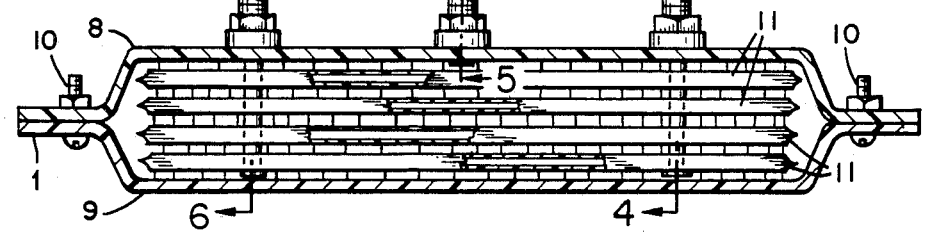
FIG. 3 is a cross-sectional view taken along line 3—3 of FIG. 1.

FIG. 3 is a cross-sectional view of FIG. 1 along line 3—3 which shows a housing 1 containing therein a number of double bag units 11, each double bag unit having a first membrane bag within a second membrane bag as will be described below. These double bag units 11 can be connected either in series or parallel via inlets 2 and 4. Inlets 2 and 4 each having a hollow post which extends through both the first membrane bag and the second membrane bag of each double unit 11 in flow communication with selected cell and nutrient or gas chambers.

Figure 4:
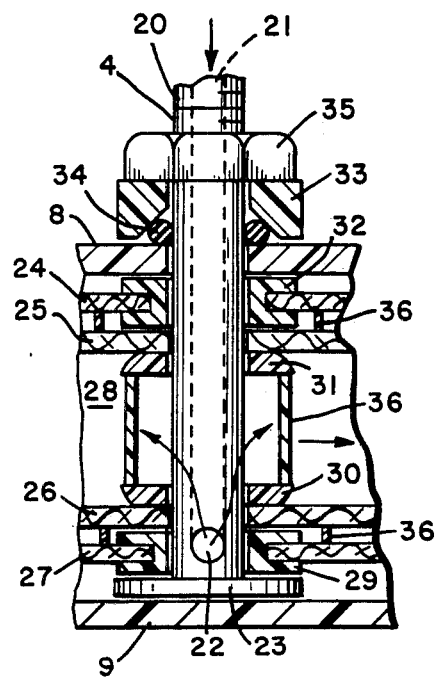
FIG. 4 is a cross-sectional view of an inlet in flow communication with a third chamber.

FIG. 4 is a cross-sectional view of inlet 4 across line 4—4 of FIG. 3. However, for representational purposes FIG. 4 only shows the use of a single double bag membrane 11, but numerous double bag units may also be used. Thus, FIG. 4 describes an inlet 4 which includes a hollow post 20 which extends through top plate 8 of the housing 1, a first membrane wall 24 of the second membrane bag, a first membrane wall 25 of the first membrane bag, a second membrane wall 26 of the first membrane bag, and a second membrane wall 27 of the second membrane bag; such that a third chamber 28 formed between the interior surfaces of the first and second membrane walls 25 and 26 of the first membrane bag.

In order to restrict the flow from inlet 4 via hollow portion 21 to a third chamber 28 the following sequence of gaskets and seals can be used. Gasket 29 is disposed between base 23 and membrane wall 26 in a liquid and gas tight configuration, wherein membrane wall 27 is embedded securely in gasket 29. Seal 30 is disposed within a third chamber 28 on the exterior surface of membrane wall 26 so as to prevent leakage either into or out of third chamber 28. Similarly, seal 31 is provided on the interior surface of membrane wall 25 also to prevent leakage into chamber 28. Gasket 32 being disposed between the exterior surface of wall 25 and the interior surface of the top plate 8 of housing 1, wherein membrane wall 24 is embedded securely in gasket 32. Gasket 33 and O-ring 34 are disposed on the exterior surface of the top plate 8 of housing 1, such that nut 35 permits sufficient tighting of inlet 4 to restrict the flow there-through into third chamber 28. Spacers 36 are for representational purposes only and are normally a plastic vexar grid which prevents membrane walls 24, 25, 26 and 27 from collapsing upon each other. The spacers 36 thereby permit continuous flow through chambers of predetermined sizes.

The configuration of FIG. 4 may be used to introduce either oxygen or nutrient into this cell culturing device depending upon the characteristics of membrane walls 25 and 26.

FIG. 4 can also be used to describe outlet 5 except that the flow would be opposite to that of the direction of the arrows as shown therein.

Figure 5:
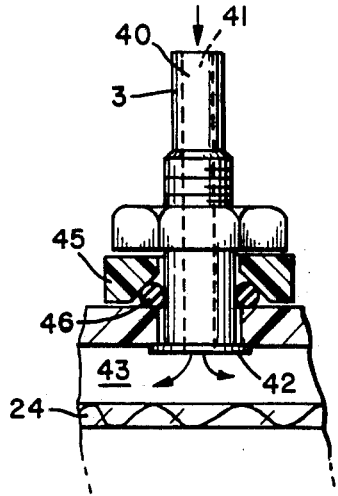
FIG. 5 is a cross-sectional view of an inlet in flow communication with a first chamber.

FIG. 5 is a cross-sectional view of inlet 3 along line 5—5 of FIG. 3. FIG. 5 describes inlet 3 having tube 40 with hollow portion 41 and base 42. Inlet 3 is used for introduction of either gas or nutrient into a first chamber 43. First chamber 43 is defined by that portion enclosed between the interior of top plate 8 of housing 1 and the exterior surface of membrane wall 24 of the second membrane bag. Inlet 3 is gas and air tight due to the disposition of gasket 45 and O-ring 46 between nut 44 and top plate 8. In accordance with FIG. 5 gas or nutrient may be introduced into first chamber 43 via hole 41 without contamination or leakage of other chambers therein.

FIG. 5 can also be used to describe outlet 6 except that the flow would be opposite to that of the direction of the arrows as shown therein.

Figure 6:
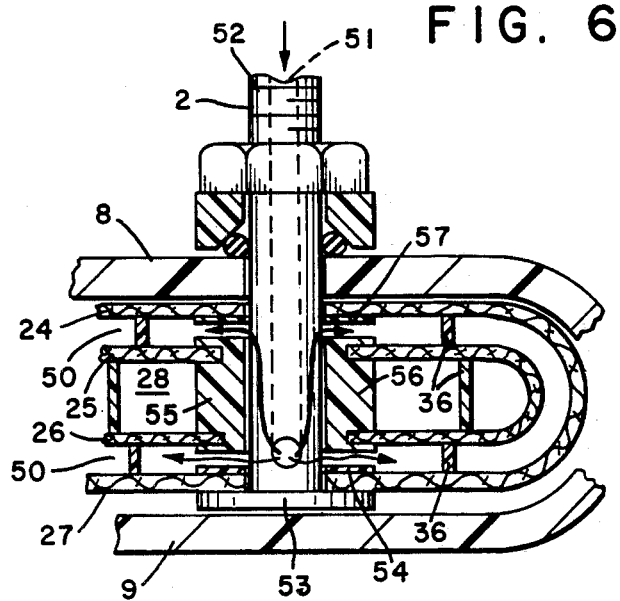
FIG. 6 is a cross-sectional view of an inlet in flow communication with a second chamber.

FIG. 6 depicts a cross-sectional view of inlet 2 across line 6—6 of FIG. 3. Inlet 2 is used to deliver cells into a second chamber 50 via a hollow portion 51 of tube 52 in the direction of the arrows as shown. The second chamber 50 is formed between a first membrane wall 24 of the second membrane bag and a first membrane wall 25 of the first membrane bag.

In order to restrict the flow from inlet 2 via hollow portion 51 to second chamber 50 the following sequence of gaskets and seals can be used. The second membrane wall 27 is disposed gas and liquid tight between base 53 and seal 54. Seal 54 being disposed on the interior surface of second membrane wall 24 of the second membrane bag. Membrane walls 25 and 26 of the first membrane bag are securely embedded into gaskets 55 and 56 such that no flow from inlet 2 enters a third chamber 28. Seals 57 are disposed on the interior surface of first membrane wall 24 such as to prevent any leakage or contamination of second chamber 50.

FIG. 6 also depicts the structural design of outlet 7, except that the arrows therein would be pointed in the opposite direction.

FIG. 7 is a top planner view of a double bag 66 according to the present invention having inlet ports 60 and 61, and outlet ports 62 and 63 in flow communication with the inlet ports, respectively. Inlet port 60 is connected to inlet 4 and inlet port 61 is connected to inlet 2.

Figure 7A:
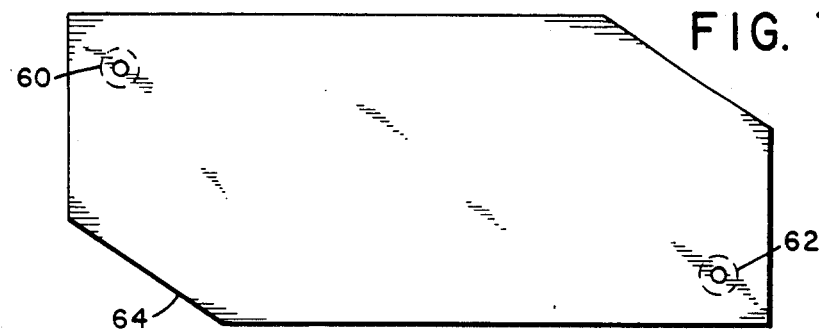
FIG. 7a is a top planner view of a first bag according to the present invention.

FIG. 7a discloses a first bag 64 which is disposed within second bag 65 to provide for a double bag 66. First bag 64 having inlet port 60 and outlet port 62 for flow-through communication with inlet 4 and outlet 5.

FIG. 8 is a cross-sectional view of a double bag 66 shown in FIG. 7 across line 8—8. FIG. 8 describes a first bag 64 and a second bag 65 forming double bag 66. Spacers 67 are disposed within the first and second bags to provide predetermined distances from the walls thereof. First bag 64 and second bag 65 are formed of either gas permeable, liquid impermeable membrane material or microfiltration or ultrafiltration membrane material and are formed into bags by heat sealing the ends thereof a shown in FIG. 8A.

FIG. 9 is a top right perspective view of an embodiment according to the present invention wherein individual units of housing 1 may be uniformly disposed on shelf 80 for connecting numerous units of housing 1 in series or parallel.

Figure 10:
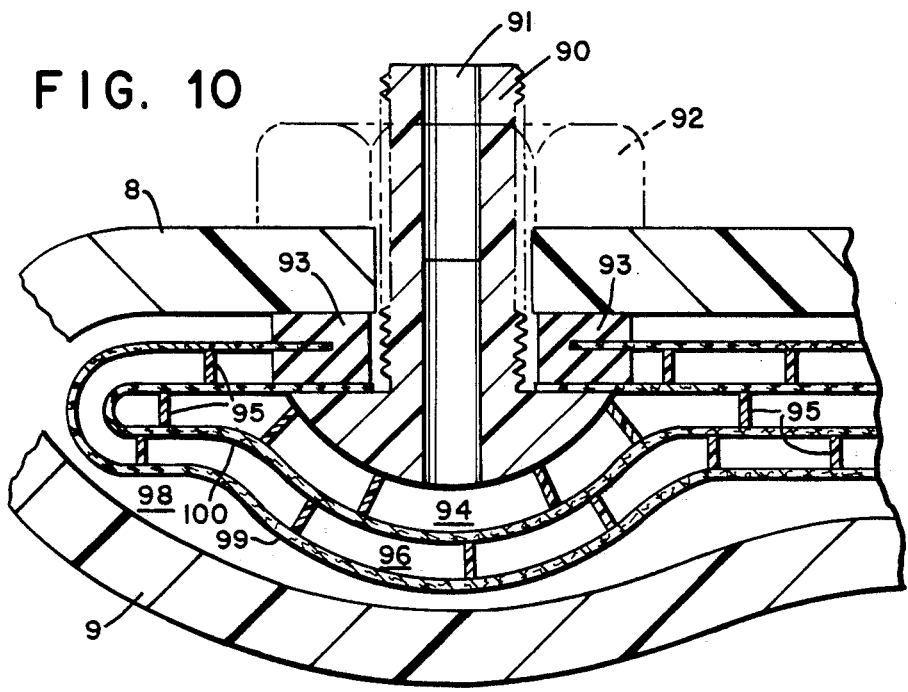
FIG. 10 is a cross-sectional view of an additional embodiment of an inlet according to the present invention.
Figure 11:
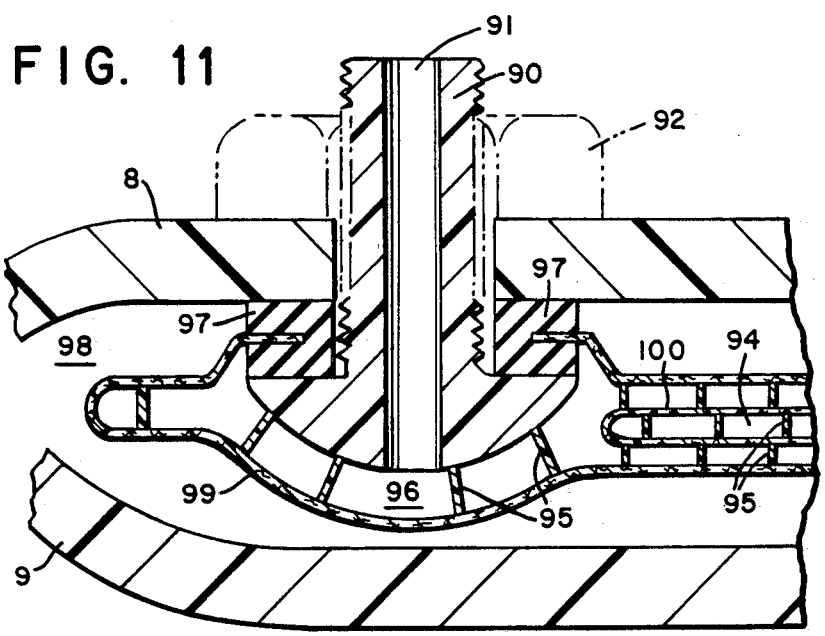
FIG. 11 is a cross-sectional view of a nylon screw according to the present invention.

FIGS. 10 and 11 show another embodiment of the present invention wherein a nylon screw 90 may be used in place of tubes 20, 40 and 52 at the inlets and outlets. A hole 91 is drilled through nylon screw 90 for flow communication with selected chambers. Nut 92 secures nylon screw 90 to the housing such that gaskets 93 and 97 maintain a liquid and air tight configuration between chambers 94 and 96. FIG. 10 describes the use of nylon screw 90 for flow communication from the inlet or outlet to a third chamber 94. Spacers 95 are provided to maintain a predetermined distance between the membrane bags. FIG. 11 provides for the use of nylon screw 90 for flow-through communication to a second chamber 96 formed between the interior wall of membrane 99 and the exterior wall of membrane 100. Although not shown in the drawing a nylon screw 90 may also be disposed directly in top plate 8 of housing 1 to permit flow communication between inlet 3 and first chamber 98.

It is also envisioned that double membrane bag 66 may be rolled into a spiral shape for conservation of space and still be capable of cell culturing.

What is claimed is:

1. An apparatus for growing cells comprising:
   a first membrane forming a first bag;
   a second membrane forming a second bag containing therein said first bag;
   a housing which encases said first and second bags;
   a first inlet disposed in said housing such that it is only in flow communication with a first chamber defined between the interior surface of said housing and the exterior surface of said second bag;
   a second inlet disposed in said housing such that it is only in flow communication with a second chamber defined between the exterior surface of said first bag and the interior surface of said second bag;
   a third inlet disposed in said housing such that it is only in flow communication with a third chamber defined within the interior surface of said first bag;
   a first outlet disposed in said housing such that it is only in flow communication with said first chamber;
   a second outlet disposed in said housing such that it is only in flow communication with said second chamber; and
   a third outlet disposed in said housing such that it is only in flow communication with said third chamber.

2. The apparatus according to claim 1, wherein spacers are disposed with said first bag and said second bag so as to maintain predetermined distances between the interior surfaces of said first bag and between the interior surface of said second bag and the exterior surface of said first bag.

3. The apparatus according to claim 2, wherein the spacers used in the first and second bags are plastic vexar grids which permit continuous flow there through.

4. The apparatus according to claim 1, wherein the ends of both the first and second membranes are sealed together to form a double bag having said first bag enclosed within said second bag.

5. The apparatus according to claim 4, wherein said double bag is in a spiral configuration such that it may be inserted into said housing, said housing being in the form of a tube or the like for containing said double bag.

6. The apparatus according to claim 1, wherein said first membrane is either a microfiltration or ultrafiltration membrane and said second membrane is a gas permeable, liquid impermeable membrane.

7. The apparatus according to claim 6, wherein said gas permeable, liquid impermeable membrane is a dimethyl silicone gas membrane.

8. The apparatus according to claim 6, wherein oxygen or air is introduced to said first chamber via said first inlet; cells are introduced into said second chamber via said second inlet; and cell nutrients are introduced into said third chamber via said third inlet.

9. The apparatus according to claim 8, wherein said oxygen or air is discharged from said first chamber via said first outlet; cells are discharged from said second chamber via said second outlet; and cell nutrients and by-products from the cells are discharged from said third chamber via said third outlet.

10. The apparatus according to claim 1, wherein said first membrane is a gas permeable, liquid impermeable membrane and said second membrane is either a microfiltration or ultrafiltration membrane.

11. The apparatus according to claim 10, wherein said gas permeable, liquid impermeable membrane is a dimethyl silicone gas membrane.

12. The apparatus according to claim 10, wherein cell nutrients are introduced into said first chamber via said first inlet; cells are introduced into said second chamber via said second inlet; and oxygen or air is introduced into said third chamber via said third inlet.

13. The apparatus according to claim 12, wherein said cell nutrient and by-products from the cells are discharged from said first chamber via said third outlet; cells are discharged from said second chamber via said second outlet; and oxygen or air is discharged from said third chamber via said third outlet.

14. The apparatus according to claim 1, wherein the inlets and outlets are hollow tubes sealed at one end and open at the other end, said hollow tubes having an opening within a side wall thereof, said opening being near said sealed end and within said housing.

15. The apparatus according to claim 14, wherein gaskets are provided at the point where the inlets and outlets penetrate said housing, said first bag and said second bag, said gaskets being arranged such that said first inlet and outlet are only in flow communication with said first chamber, said second inlet and outlet are only in flow communication with said second chamber, and said third inlet and outlet are only in flow communication with said third chamber, whereby leakage into the other chamber is avoided.

16. The apparatus according to claim 1, wherein the inlets and outlets are nylon screws.

17. An apparatus for growing cells comprising:
a first membrane forming a first bag having a spacer material disposed within said first bag so as to maintain each side of said first bag at a predetermined distance from the opposing side;
a second membrane forming a second bag containing therein said first bag, having a spacer material disposed within said second bag so as to maintain a predetermined distance between the interior surface of said second bag and the exterior surface of said first bag, said first bag and said second bag forming a single double bag unit;
a housing encasing a series of double bag units which are in flow communication with each and every other double bag unit;
a first inlet disposed in said housing such that it is only in flow communication with a first chamber defined between the interior surface of said housing and the exterior surface of each said double bag unit encased within said housing;
a second inlet disposed in said housing such that it is only in flow communication with the second chamber of each said double bag unit encased within said housing, said second chambers defined between the exterior surfaces of said first bags and the interior surfaces of said second bags;
a third inlet disposed in said housing such that it is only in flow communication with the third chamber of each said double bag unit encased within said housing, said third chamber defined within the interior surfaces of said first bags;
a first outlet disposed in said housing such that it is only in flow communication with the first chamber of each double bag unit encased within said housing;
a second outlet disposed in said housing such that it is only in flow communication with the second chambers of each double bag unit encased within said housing; and
a third outlet disposed in said housing such that it is only in flow communication with the third chamber of each double bag unit encased within said housing.

18. A method for growing cells comprising:
introducing oxygen or air to a first inlet disposed in a housing, said housing encasing a first microfiltration or ultrafiltration membrane bag enclosed in a second gas permeable, liquid impermeable membrane bag, said first inlet being in flow communication with a first chamber defined between the interior surface of said housing and the exterior surface of said second gas permeable, liquid impermeable bag;
introducing cells to a second inlet disposed in said housing such that it is in flow communication with a second chamber defined between the exterior surface of said first microfiltration or ultrafiltration membrane bag and the interior surface of said second gas permeable, liquid impermeable membrane bag;
introducing cell nutrients to a third inlet disposed in said housing such that it is in flow communication with a third chamber defined within the interior surface of said first microfiltration or ultrafiltration membrane bag;
withdrawing depleted oxygen or air via a first outlet disposed in said housing such that it is in flow communication with said first chamber;
withdrawing cells via a second outlet disposed in said housing such that it is in flow communication with said second chamber; and
withdrawing cell nutrients and by-products of said cells via a third outlet disposed in said housing such that it is in flow communication with said third chamber.

19. A method for growing cells comprising:
introducing cell nutrients to a first inlet disposed in a housing, said housing encasing a first gas permeable, liquid impermeable membrane bag enclosed in a second microfiltration or ultrafiltration membrane bag, said first inlet being in flow communication with a first chamber defined between the interior surface of said housing and the exterior surface of said second microfiltration or ultrafiltration membrane bag;
introducing cells to a second inlet disposed in said housing such that it is in flow communication with a second chamber defined between the exterior surface of said first gas permeable, liquid impermeable membrane bag and the interior surface of said second microfiltration or ultrafiltration membrane bag; 'introducing oxygen or air to a third inlet disposed in said housing such that it is in flow communication with a third chamber defined within the interior surface of said first gas permeable, liquid impermeable membrane bag;
withdrawing cell nutrients and by-products of said cells via a first outlet disposed in said housing such that it is in flow communication with said first chamber;

withdrawing cells via a second outlet disposed in said housing such that it is in flow communication with said second chamber; and withdrawing depleted oxygen or air via a third outlet disposed in said housing such that it is in flow communication with said third chamber.

20. A method for growing cells comprising;

introducing oxygen or air to a first inlet disposed in a housing, said housing encasing a series of double bag units which are in flow communication with other double bag units, said double bag units comprising a first membrane bag disposed in a second membrane bag, said first inlet being in flow communication with a first chamber defined between the interior surface of said housing and the exterior surface of each of said double bag units encased within said housing;

introducing cells to a second inlet disposed in said housing such that it is in flow communication with a second chamber of each said double bag unit encased within said housing, said second chambers defined between the exterior surface of said first membrane bags and the interior surfaces of said second membrane bags;

introducing cell nutrients to a third inlet disposed in said housing such that it is in flow communication with the third chamber of each said double bag unit encased within said housing, said third chamber defined within the interior surface of said first membrane bags; withdrawing depleted oxygen or air via a first outlet disposed in said housing such that it is in flow communication with the first chamber of each double bag unit encased within said housing;

withdrawing cells via a second outlet disposed in said housing such that it is in flow communication with said second chambers of each double bag unit encased within said housing; and withdrawing cell nutrients and by-products of the cells via a third outlet disposed in said housing such that it is flow communication with the third chamber of each double bag unit encased within said housing.

* * * * *